(12) United States Patent
Blomqvist et al.

(10) Patent No.: US 11,564,609 B2
(45) Date of Patent: Jan. 31, 2023

(54) METHOD, APPARATUS AND COMPUTER PROGRAM FOR SYNCHRONIZING BIOPOTENTIAL SIGNALS

(71) Applicant: Nokia Technologies Oy, Espoo (FI)

(72) Inventors: Kim Blomqvist, Espoo (FI); Mikko Honkala, Espoo (FI); Kiti Müller, Helsinki (FI); Harri Lindholm, Helsinki (FI)

(73) Assignee: Nokia Technologies Oy, Espoo (FI)

( * ) Notice: Subject to any disclaimer, the term of this patent is extended or adjusted under 35 U.S.C. 154(b) by 371 days.

(21) Appl. No.: 16/759,810

(22) PCT Filed: Oct. 1, 2018

(86) PCT No.: PCT/EP2018/076573
§ 371 (c)(1),
(2) Date: Apr. 28, 2020

(87) PCT Pub. No.: WO2019/086182
PCT Pub. Date: May 9, 2019

(65) Prior Publication Data
US 2020/0305748 A1   Oct. 1, 2020

(30) Foreign Application Priority Data
Oct. 31, 2017  (EP) .................................. 17199453

(51) Int. Cl.
*A61B 5/00* (2006.01)
*A61B 5/316* (2021.01)
(Continued)

(52) U.S. Cl.
CPC .......... *A61B 5/316* (2021.01); *A61B 5/0006* (2013.01); *A61B 5/302* (2021.01); *A61B 5/318* (2021.01);
(Continued)

(58) Field of Classification Search
CPC .......... A61B 2562/0214; A61B 5/0006; A61B 5/0531; A61B 5/302; A61B 5/316;
(Continued)

(56) References Cited

U.S. PATENT DOCUMENTS

| 5,740,811 A | 4/1998 | Hedberg et al. |
|---|---|---|
| 9,101,264 B2 | 8/2015 | Acquista |

(Continued)

FOREIGN PATENT DOCUMENTS

| CN | 102448370 A | 5/2012 |
|---|---|---|
| CN | 104717919 A | 6/2015 |

(Continued)

OTHER PUBLICATIONS

Office action received for corresponding European Patent Application No. 17199453.6, dated May 23, 2022, 6 pages.

(Continued)

*Primary Examiner* — George Manuel
(74) *Attorney, Agent, or Firm* — Harrington & Smith

(57) ABSTRACT

A method, apparatus and computer program, the method comprising: receiving a first biopotential signal obtained by a first capacitive sensor; receiving a second biopotential signal obtained by a second capacitive sensor, the first capacitive sensor and the second capacitive sensor being positioned at different locations on a subject; synchronising biopotential signals obtained by the first capacitive sensor and the second capacitive sensor by applying a time adjustment to biopotential signals obtained by at least one of the first capacitive sensor or the second capacitive sensor; wherein features in at least one of the first biopotential signal and the second biopotential signal are used to synchronise the biopotential signals obtained by the first capacitive sensor and the second capacitive sensor.

20 Claims, 4 Drawing Sheets

Figure 1:
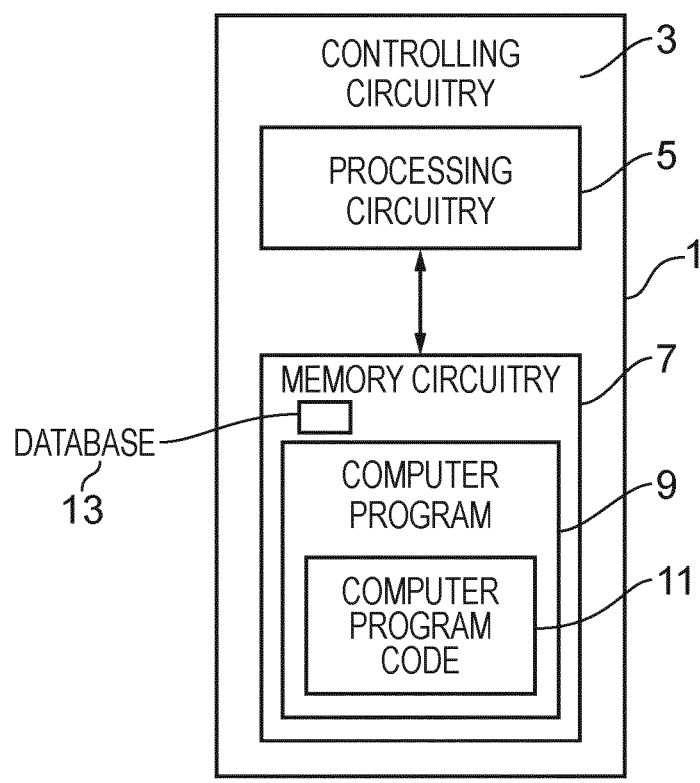

(51) Int. Cl.
| | |
|---|---|
| A61B 5/302 | (2021.01) |
| A61B 5/318 | (2021.01) |
| A61B 5/369 | (2021.01) |
| A61B 5/389 | (2021.01) |
| A61B 5/398 | (2021.01) |

(52) U.S. Cl.
CPC .............. *A61B 5/369* (2021.01); *A61B 5/389* (2021.01); *A61B 5/398* (2021.01); *A61B 5/7203* (2013.01); *A61B 2562/0214* (2013.01)

(58) Field of Classification Search
CPC ......... A61B 5/318; A61B 5/369; A61B 5/389; A61B 5/398; A61B 5/72; A61B 5/7203; C12Q 1/6883; C12Q 2600/106; C12Q 2600/112; C12Q 2600/156; C12Q 2600/172
See application file for complete search history.

(56) References Cited

U.S. PATENT DOCUMENTS

| | | | |
|---|---|---|---|
| 9,295,424 | B2 | 3/2016 | Todorov et al. |
| 2002/0045836 | A1 | 4/2002 | Alkawwas |
| 2006/0287608 | A1 | 12/2006 | Dellacorna |
| 2011/0004072 | A1 | 1/2011 | Fletcher et al. |
| 2014/0364759 | A1* | 12/2014 | Choi ................... A61B 5/7225 600/547 |
| 2015/0257647 | A1 | 9/2015 | Buck et al. |
| 2016/0151022 | A1 | 6/2016 | Berlin et al. |
| 2016/0213264 | A1 | 7/2016 | Gil et al. |
| 2017/0007146 | A1 | 1/2017 | Schulhauser et al. |

FOREIGN PATENT DOCUMENTS

| | | |
|---|---|---|
| DE | 102016203338 A1 | 9/2017 |
| EP | 1815784 A1 | 8/2007 |
| WO | 2010/136946 A2 | 12/2010 |
| WO | 2016/123206 A1 | 8/2016 |
| WO | 2016/135661 A1 | 9/2016 |

OTHER PUBLICATIONS

"CardioSecur 22-Lead Mobile ECG Enables 360-Degree View of the Heart", DAIC, Retrieved on Apr. 21, 2020, Webpage available at : https://www.dicardiology.com/product/cardiosecur-22-lead-mobile-ecg-enables-360-degree-view-heart.

"Enobio 32", Neuroelectrics, Retrieved on Apr. 21, 2020, Webpage available at : http://www.neuroelectrics.com/products/enobio/enobio-32/.

"Raising an alarm, doctors fight to yank hospital ICUs into the modern era", STAT, Retrieved on Apr. 21, 2020, Webpage available at : https://www.statnews.com/2016/09/07/hospital-icu-modernize/.

Choi et al., "Reduction of Motion Artifacts and Improvement of R Peak Detecting Accuracy Using Adjacent Non-Intrusive ECG Sensors", Sensors, vol. 16, No. 5, May 2016, pp. 1-18.

Hassanalieragh et al., "Health Monitoring and Management Using Internet-of-things (IoT) Sensing with Cloudbased Processing: Opportunities and Challenges", IEEE International Conference on Services Computing, Jun. 27, Jul. 2, 2015, pp. 285-292.

Coakley et al., "Alignment of Noisy Signals", IEEE Transactions on Instrumentation and Measurement, vol. 50, No. 1, Feb. 2001, pp. 141-149.

Hartmann, "Reconstruction of Missing Cardiovascular Signals Using Adaptive Filtering", Computing in Cardiology, Sep. 26-29, 2010, 4 pages.

Wang et al., "Wireless Sensor-based Smart-clothing Platform for ECG Monitoring", Hindawi Publishing Corporation, Computational and Mathematical Methods in Medicine, vol. 2015, 2015, 8 pages.

"Dynamic Time Warping", Wikipedia, Retrieved on Apr. 21, 2020, Webpage available at : https://en.wikipedia.org/wiki/Dynamic_time_warping.

Extended European Search Report received for corresponding European Patent Application No. 17199453.6, dated Apr. 30, 2018, 8 pages.

International Search Report and Written Opinion received for corresponding Patent Cooperation Treaty Application No. PCT/EP2018/076573, dated Nov. 29, 2018, 14 pages.

Office action received for corresponding Chinese Patent Application No. 201880070988.5, dated Jun. 22, 2022, 8 pages of office action and no page of translation available.

* cited by examiner

METHOD, APPARATUS AND COMPUTER PROGRAM FOR SYNCHRONIZING BIOPOTENTIAL SIGNALS

RELATED APPLICATION

This application claims priority to PCT Application No. PCT/EP2018/076573, filed on Oct. 1, 2018, which claims priority to European Application No 17199453.6, filed on Oct. 31, 2017, each of which is incorporated herein by reference in its entirety.

TECHNOLOGICAL FIELD

Examples of the disclosure relate to a method, apparatus and computer program for synchronizing biopotential signals. In particular they relate to a method, apparatus and computer program for synchronizing biopotential signals obtained by a plurality of capacitive sensors.

BACKGROUND

Capacitive sensors can be used to detect biopotential signals such as ECG (electrocardiogram) or EEG (electroencephalogram) signals. Such sensing systems may comprise a plurality of sensors which may be positioned at different locations on a subject's body.

BRIEF SUMMARY

According to various, but not necessarily all, examples of the disclosure there may be provided a method comprising: receiving a first biopotential signal obtained by a first capacitive sensor; receiving a second biopotential signal obtained by a second capacitive sensor, the first capacitive sensor and the second capacitive sensor being positioned at different locations on a subject; synchronising biopotential signals obtained by the first capacitive sensor and the second capacitive sensor by applying a time adjustment to biopotential signals obtained by at least one of the first capacitive sensor or the second capacitive sensor; wherein features in at least one of the first biopotential signal and the second biopotential signal are used to synchronise the biopotential signals obtained by the first capacitive sensor and the second capacitive sensor.

Synchronising the biopotential signals may comprise determining a delay between the first biopotential signal and the second biopotential signal.

Synchronising the biopotential signals may comprise combining the first biopotential signal and the second biopotential signal and adjusting the time alignment of the biopotential signals to provide a combined signal comprising features. The method may comprise using a machine learning process to recognise the identifiable features.

The biopotential signals that are synchronised may comprise the first biopotential signal and the second biopotential signal.

The biopotential signals that are synchronised comprise further biopotential signals detected by the first capacitive sensor and the second capacitive sensor. The first biopotential signal and the second biopotential signal may comprise information indicative of a first type of biopotential and the further biopotential signals detected by the first capacitive sensor and the second capacitive sensor comprise information indicative of a second different type of biopotential. The first biopotential signal and the second biopotential signal may comprise electrocardiogram signals and the further biopotential signals comprise at least one of; electroencephalogram signals, electro-oculogram signals, electronystagmogram signals, electromyogram signals, electroneurogram signals, or skin potentials.

The method may comprise causing processing of the synchronised biopotential signals wherein the processing comprises at least one of; removing noise from one or more of the biopotential signals, reconstructing at least part of the one or more biopotential signals. The machine learning process may be used to reconstruct at least part of the one or more biopotential signals.

The biopotential signals obtained by the first capacitive sensor and the second capacitive sensor may be received via wireless communication links.

The biopotential signals may be obtained from more than two capacitive sensors.

The method may comprise providing a control signal for at least one of the capacitive sensors wherein the control signal causes the at least one capacitive sensor to be active for a first time period and inactive for a second time period.

The method may comprise providing control signals to the capacitive sensors so that different capacitive sensors are arranged to detect the biopotentials at different times.

According to various, but not necessarily all, examples of the disclosure there may be provided an apparatus comprising: means for receiving a first biopotential signal obtained by a first capacitive sensor; means for receiving a second biopotential signal obtained by a second capacitive sensor, the first capacitive sensor and the second capacitive sensor being positioned at different locations on a subject; means for synchronising biopotential signals obtained by the first capacitive sensor and the second capacitive sensor by applying a time adjustment to biopotential signals obtained by at least one of the first capacitive sensor or the second capacitive sensor; wherein features in at least one of the first biopotential signal and the second biopotential signal are used to synchronise the biopotential signals obtained by the first capacitive sensor and the second capacitive sensor.

According to various, but not necessarily all, examples of the disclosure there may be provided an apparatus comprising: processing circuitry; and memory circuitry including computer program code, the memory circuitry and the computer program code configured to, with the processing circuitry, cause the apparatus to: receive a first biopotential signal obtained by a first capacitive sensor; receive a second biopotential signal obtained by a second capacitive sensor, the first capacitive sensor and the second capacitive sensor being positioned at different locations on a subject; synchronise biopotential signals obtained by the first capacitive sensor and the second capacitive sensor by applying a time adjustment to biopotential signals obtained by at least one of the first capacitive sensor or the second capacitive sensor; wherein features in at least one of the first biopotential signal and the second biopotential signal are used to synchronise the biopotential signals obtained by the first capacitive sensor and the second capacitive sensor.

According to various, but not necessarily all, examples of the disclosure there may be provided a computer program comprising computer program instructions that, when executed by processing circuitry, causes receiving a first biopotential signal obtained by a first capacitive sensor; receiving a second biopotential signal obtained by a second capacitive sensor, the first capacitive sensor and the second capacitive sensor being positioned at different locations on a subject; synchronising biopotential signals obtained by the first capacitive sensor and the second capacitive sensor by applying a time adjustment to biopotential signals obtained by at least one of the first capacitive sensor or the second capacitive sensor; wherein features in at least one of the first biopotential signal and the second biopotential signal are used to synchronise the biopotential signals obtained by the first capacitive sensor and the second capacitive sensor.

According to various, but not necessarily all, examples of the disclosure there are provided examples as claimed in the appended claims.

BRIEF DESCRIPTION

Figure 2:
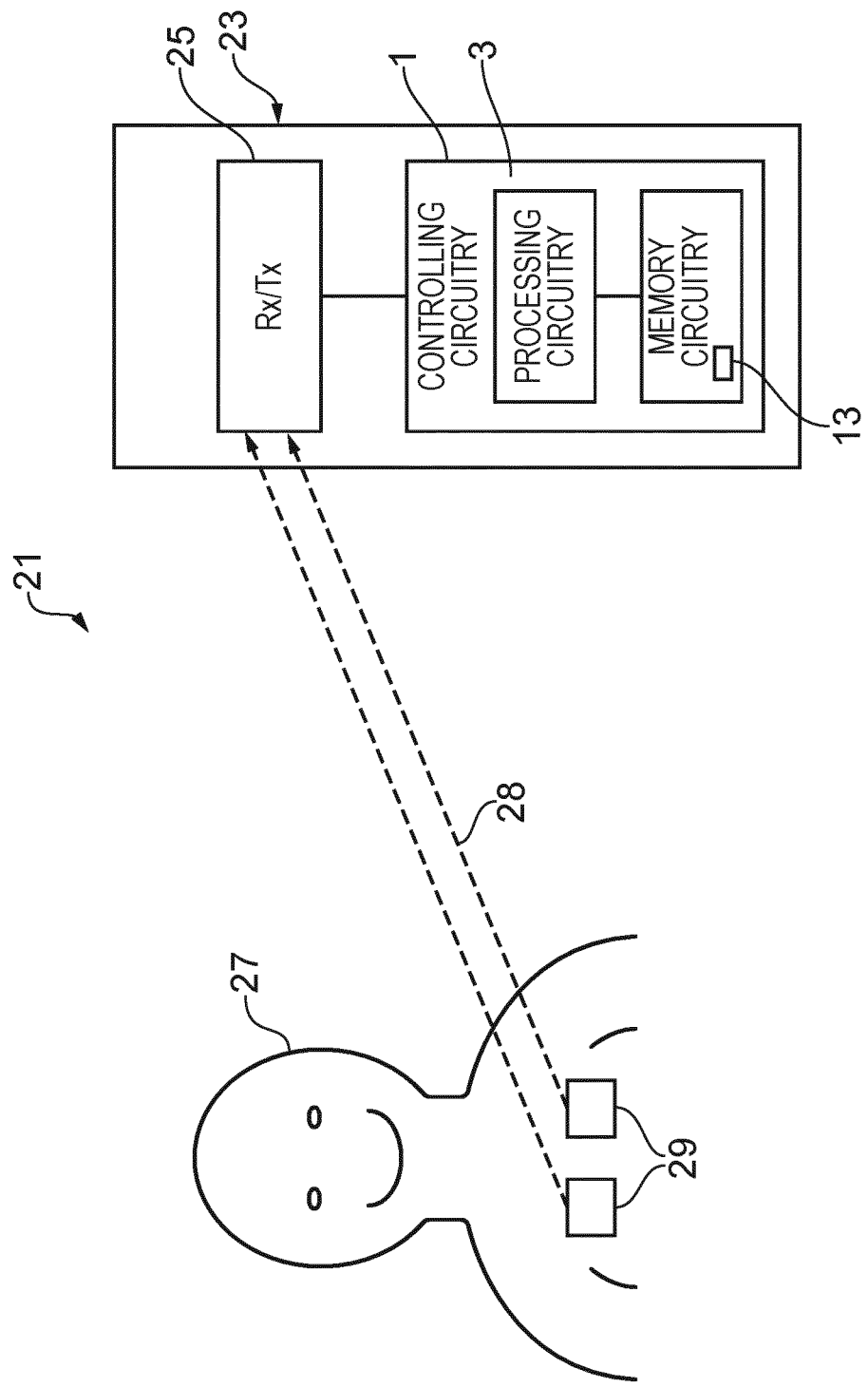
Figure 3:
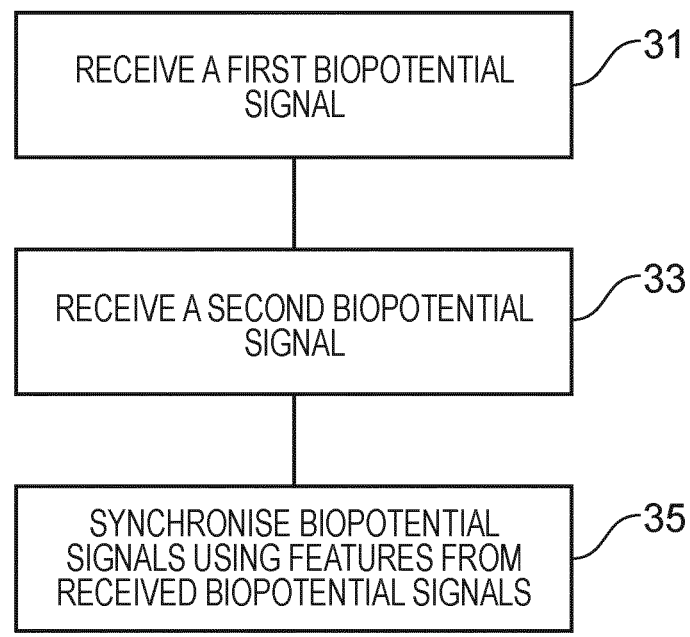
Figure 4:
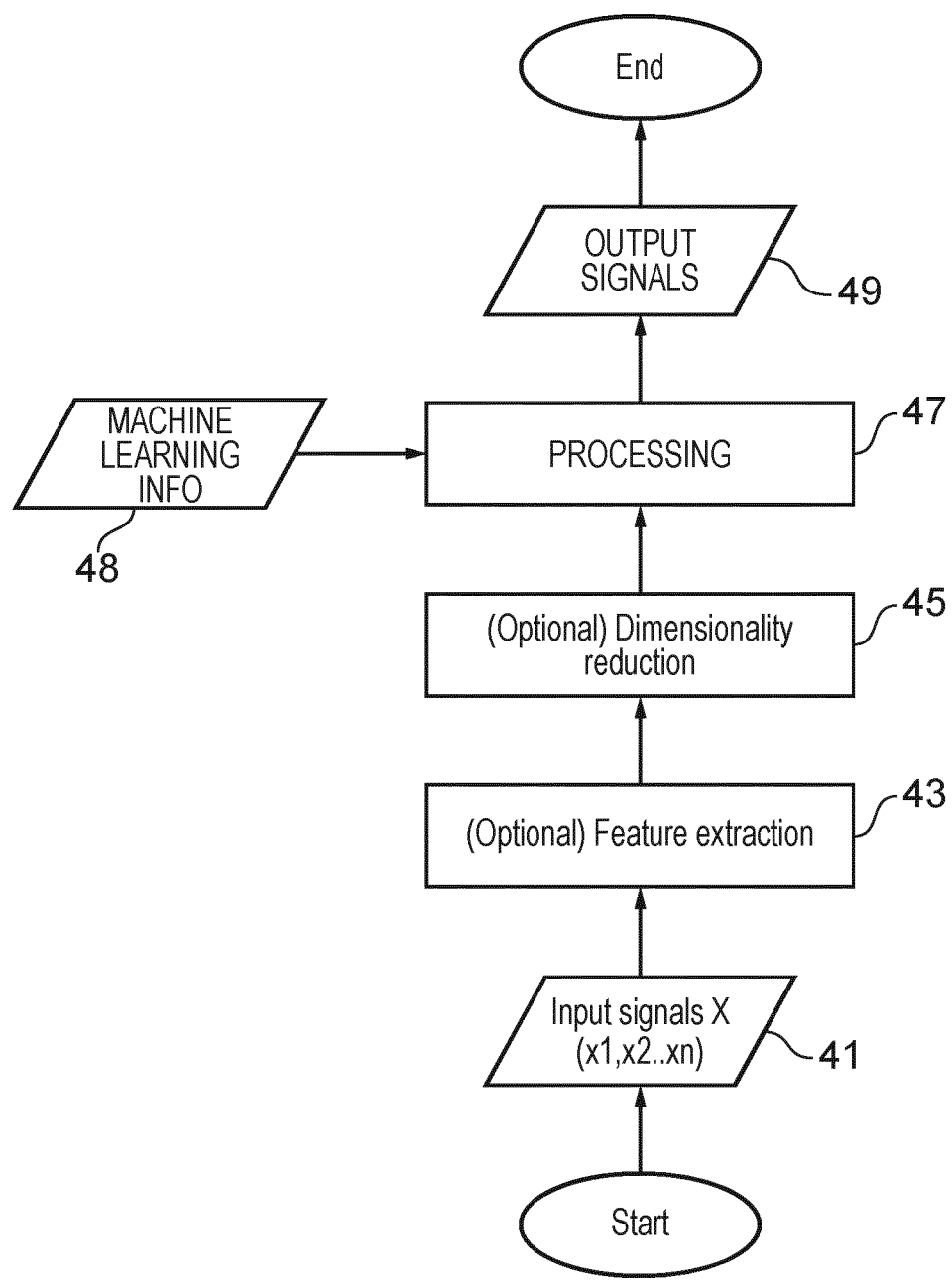

For a better understanding of various examples that are useful for understanding the detailed description, reference will now be made by way of example only to the accompanying drawings in which:

FIG. 1 illustrates an apparatus;
FIG. 2 illustrates a system;
FIG. 3 illustrates a method; and
FIG. 4 illustrates another method.

DETAILED DESCRIPTION

Examples of the disclosure relate to methods, apparatus and computer programs which may be used to synchronize biopotential signals obtained from capacitive electrodes. The methods, apparatus and computer programs and computer programs can be used with wireless electrodes. The wireless electrodes may be easier and more convenient to attach to a subject than electrodes which are coupled together by one or more wires or cables.

FIG. 1 schematically illustrates an apparatus 1 which may be used to implement examples of the disclosure.

The apparatus 1 illustrated in FIG. 1 may be a chip, a chip-set or any other suitable arrangement. In some examples the apparatus 1 may be provided within any suitable device such as a processing device or a communications device.

The apparatus 1 comprises controlling circuitry 3. The controlling circuitry 3 may provide means for controlling an electronic device such as processing device or a communications device. The controlling circuitry 3 may also provide means for performing the methods, or at least part of the methods, of examples of the disclosure.

The controlling circuitry 3 comprises processing circuitry 5 and memory circuitry 7. The processing circuitry 5 may be configured to read from and write to the memory circuitry 7. The processing circuitry 5 may comprise one or more processors. The processing circuitry 5 may also comprise an output interface via which data and/or commands are output by the processing circuitry 5 and an input interface via which data and/or commands are input to the processing circuitry 5.

The memory circuitry 7 may be configured to store a computer program 9 comprising computer program instructions (computer program code 11) that controls the operation of the apparatus 1 when loaded into processing circuitry 5. The computer program instructions, of the computer program 9, provide the logic and routines that enable the apparatus 1 to perform the example methods described. The processing circuitry 5 by reading the memory circuitry 7 is able to load and execute the computer program 9.

In examples of the disclosure the memory circuitry 7 is arranged to store one or more databases 13. The databases 13 may be used to store information that can be used to enable a plurality of biopotential signals to be synchronised. In some examples the databases 13 may comprise reference signals that can be compared to biopotential signals obtained by a plurality of capacitive electrodes to enable the biopotential signals to be synchronised. The information stored in the databases 13 may comprise information which enables a machine learning algorithm to be used to synchronise the biopotential signals.

The computer program 9 may arrive at the apparatus 1 via any suitable delivery mechanism. The delivery mechanism may be, for example, a non-transitory computer-readable storage medium, a computer program product, a memory device, a record medium such as a compact disc read-only memory (CD-ROM) or digital versatile disc (DVD), or an article of manufacture that tangibly embodies the computer program. The delivery mechanism may be a signal configured to reliably transfer the computer program 9. The apparatus may propagate or transmit the computer program 9 as a computer data signal. In some examples the computer program code 11 may be transmitted to the apparatus 1 using a wireless protocol such as Bluetooth, Bluetooth Low Energy, Bluetooth Smart, 6LoWPan (IP$_v$6 over low power personal area networks) ZigBee, ANT+, near field communication (NFC), Radio frequency identification, wireless local area network (wireless LAN) or any other suitable protocol.

Although the memory circuitry 7 is illustrated as a single component in the figures it is to be appreciated that it may be implemented as one or more separate components some or all of which may be integrated/removable and/or may provide permanent/semi-permanent/dynamic/cached storage.

Although the processing circuitry 5 is illustrated as a single component in the figures it is to be appreciated that it may be implemented as one or more separate components some or all of which may be integrated/removable.

References to "computer-readable storage medium", "computer program product", "tangibly embodied computer program" etc. or a "controller", "computer", "processor" etc. should be understood to encompass not only computers having different architectures such as single/multi-processor architectures, Reduced Instruction Set Computing (RISC) and sequential (Von Neumann)/parallel architectures but also specialized circuits such as field-programmable gate arrays (FPGA), application-specific integrated circuits (ASIC), signal processing devices and other processing circuitry. References to computer program, instructions, code etc. should be understood to encompass software for a programmable processor or firmware such as, for example, the programmable content of a hardware device whether instructions for a processor, or configuration settings for a fixed-function device, gate array or programmable logic device etc.

As used in this application, the term "circuitry" refers to all of the following:
(a) hardware-only circuit implementations (such as implementations in only analog and/or digital circuitry) and
(b) to combinations of circuits and software (and/or firmware), such as (as applicable): (i) to a combination of processor(s) or (ii) to portions of processor(s)/software (including digital signal processor(s)), software, and memory(ies) that work together to cause an apparatus, such as a mobile phone or server, to perform various functions) and
(c) to circuits, such as a microprocessor(s) or a portion of a microprocessor(s), that require software or firmware for operation, even if the software or firmware is not physically present.

This definition of "circuitry" applies to all uses of this term in this application, including in any claims. As a further example, as used in this application, the term "circuitry"

would also cover an implementation of merely a processor (or multiple processors) or portion of a processor and its (or their) accompanying software and/or firmware. The term "circuitry" would also cover, for example and if applicable to the particular claim element, a baseband integrated circuit or applications processor integrated circuit for a mobile phone or a similar integrated circuit in a server, a cellular network device, or other network device.

FIG. 2 schematically illustrates an example system 21 which may be used to implement embodiments of the disclosure. The example system 21 comprises a processing device 23 and a plurality of capacitive sensors 29.

The processing device 23 comprises an apparatus 1 comprising controlling circuitry 3 which may be as described above. In the example of FIG. 2 the memory circuitry 7 comprises a database 13. In other examples one or more databases 13 may be stored in one or more different devices. The processing device 23 may be arranged to communicate with the one or more different devices so as to enable the one or more databases 13 to be accessed as needed.

The processing device 23 also comprises one or more transceivers 25. In the example of FIG. 2 the transceiver is shown as a single component. It is to be appreciated that separate transmitters and receivers may be provided in some processing devices 23 in other examples of the disclosure.

The transceiver 25 may comprise any means which enables a communication link 28 to be established between the processing device 23 and the plurality of capacitive sensors 29. The transceivers 25 may enable wireless communication links to be established. The wireless communication links could be any suitable type of communication links such as Bluetooth, Bluetooth Low Energy, Bluetooth Smart, 6LoWPan ($IP_v6$ over low power personal area networks) ZigBee, ANT+, Radio frequency identification, wireless local area network (wireless LAN) or any other suitable types of wireless communication links.

The system 21 also comprises a plurality of capacitive sensors 29. In the example of FIG. 2 two electrodes are shown however it is to be appreciated that any number of capacitive sensors 29 could be used in other examples of the disclosure.

The capacitive sensors 29 are positioned on the body of a subject 27. In the example of FIG. 2 the subject 27 is a person however examples of the disclosure could also be used for animals. The capacitive sensors 29 may be positioned on any suitable location on the subject 27. The location of the capacitive sensors 29 may be determined by the biopotential signals that the capacitive sensors 29 are arranged to detect. For instance, where the capacitive sensors 29 are arranged to detect an ECG signal the capacitive sensors 29 may be positioned on the subject's 27 chest and where the capacitive sensors 29 are arranged to detect an EEG signal the capacitive sensors 29 may be positioned on the subject's 27 head.

The capacitive sensors 29 may comprise any means which may be arranged to capacitively sense a biopotential signal from the subject's body. The capacitive sensors 29 may be arranged so that the conductive portions of the capacitive sensors 29 are not in direct electrical contact with the subject's body.

The capacitive sensors 29 may be wireless capacitive sensors 29. In examples of the disclosure there might be no cables or wires between any of the capacitive sensors 29 on the subject 27. Each of the plurality of capacitive sensors 29 may therefore be standalone capacitive sensors 29 which can operate independently so that each capacitive sensor 29 measures a biopotential signal independently of the other capacitive sensors 29.

The capacitive sensors 29 may also comprise one or more transceivers which enable the capacitive sensors 29 to establish a wireless communication link between the capacitive sensors 29 and the processing device 23. This enables the system 21 to be arranged without any wires or cables needed to connect the capacitive sensors 29 and processing device 23 together. This may make the system 21 easier and more convenient to use as there are no cables which might restrict the possible positions of the capacitive sensors 29. In other examples a partially wired system 21 may be used. The partially wired system 21 may comprise some wires connecting one or more of the sensors 29 to other components within the system 21. The partially wired system 21 might not comprise any wires directly between sensors 21.

The biopotential signals that are measured by the capacitive sensors 29 may comprise any time varying electrical signal that is generated by the subject 27. The biopotential signal may comprise an autonomic signal. The autonomic signal may be controlled subconsciously by the subject 27. In some examples the biopotential signals may comprise electrical signals that are generated within the subject's body by the user's heartbeat. In some examples the biopotential signals could comprise electrical activity of the user's brain or other parts of their nervous system. The biopotential signal could comprise at least one of an electrocardiogram signal, electroencephalogram signal, electromyogram signal, electrooculogram signal, electrogastrogram signal, electonystagmogram signal, skin potential signal or any other suitable biopotential signal.

In the example system 21 of FIG. 2 the processing device 23 has established a communication link 28 directly with each of the capacitive sensors 29. In this example there are no intervening elements between the capacitive sensors 29 and the processing device 23. In other examples, one or more additional devices could be provided between the capacitive sensors 29 and the processing device 23. For instance the system could comprise a communication device. The capacitive sensors 29 may be arranged to transmit the biopotential signals to the communication device via any suitable means. The communication device could then transmit the biopotential signals to the processing device 23.

In the example of FIG. 2 the processing device 23 is provided as a separate device to any of the sensors 29. Each of the sensors 29 is arranged to provide signals to the processing device 23 via the communication link 28. In other examples one or more sensors 29 could be provided within the processing device 23. In such examples the sensors 29 which are not part of the processing device 23 may provide signals via a communication link 28 while the sensors 29 which are provided within the processing device 23 do not need such a communication link 28.

FIG. 3 illustrates a method for synchronizing biopotential signals that are obtained using the capacitive sensors 29. The method may be implemented using apparatus 1 and systems 21 as described above. In some examples the method may be performed by a single processing device 23. In other examples the method mat be performed by two or more distributed processing devices 23.

The method comprises receiving, at block 31, a first biopotential signal obtained by a first capacitive sensor 29 and at block 33, receiving a second biopotential signal obtained by a second capacitive sensor 29. The first capacixtive sensor 29 and the second capacitive sensor 29 are positioned at different locations on a subject 27.

The first capacitive sensor 29 and the second capacitive sensor 29 may be operating independently of each other. There might be no wires or cables connecting the respective capacitive sensors 29. The capacitive sensors 29 may be arranged to communicate with the processing device 23 however the capacitive sensors 29 may be arranged so that there is no direct communication between the capacitive sensors 29 themselves.

In examples of the disclosure the biopotential signals obtained by the first capacitive sensor 29 and the second capacitive sensor 29 are received via wireless communication links 28. In examples of the disclosure the processing device 23 may establish a separate communication link 28 with each of the capacitive sensors 29. This may ensure that the respective capacitive sensors 29 can operate independently of each other.

At block 35 the method comprises synchronising biopotential signals obtained by the first capacitive sensor 29 and the second capacitive sensor 29 by applying a time adjustment to biopotential signals obtained by at least one of the first capacitive sensor 29 or the second capacitive sensor 29. Features in at least one of the first biopotential signal and the second biopotential signal are used to synchronise the biopotential signals obtained by the first capacitive sensor 29 and the second capacitive sensor 29.

Other suitable processes may be used to synchronise the biopotential signals. In some examples synchronising the biopotential signals comprises determining a delay between the first biopotential signal and the second biopotential signal. In such examples the delay may be calculated or estimated and information indicative of the delay may be stored in the memory circuitry 7. The information indicative of the delay can then be retrieved when needed to synchronise biopotential signals obtained by the capacitive sensors 29.

Other suitable methods may be used to determine the delay between the respective biopotential signals. In some examples the process of determining the delay may comprise cross collating the respective biopotential signals and comparing the delay between features in the signals. The features could comprise features of the biopotential signals. For example they could comprise the distinctive maxima and minima of an ECG signal. In some examples the features could comprise noise that is present in all of the bio potential signals obtained by the capacitive sensors 29.

In some examples the biopotential signals could be synchronised without explicitly calculating or estimating the delay. For instance, in some examples synchronising the biopotential signals comprises combining the first biopotential signal and the second biopotential signal and adjusting the time alignment of the biopotential signals to provide a combined signal comprising identifiable features. The identifiable features may comprise any features within the signals that can be recognised by the processing circuitry 5. For example, the identifiable features may comprise any suitable patterns, shape or sequences within the biopotential signals In such examples a machine learning process may be used to recognise the identifiable features. The machine learning process may comprise retrieving information stored in one or more databases 13 and comparing the combined biopotential signals with the retrieved information. The combined biopotential signals may be considered to be synchronised when the combined signals correspond to the retrieved information. The combined biopotential signals may correspond to the retrieved information when one or more identifiable features in the combined signals match, or are similar to features from signals stored in the database 13.

In some examples the biopotential signals that are synchronised comprise the first biopotential signal and the second biopotential signal. For instance the first biopotential signal and the second biopotential signal may be stored in the memory circuitry and may be synchronised by the processing device 23. The synchronisation may be performed in real time. For example, it may be performed by the processing device 23 while the capacitive sensors 29 are obtaining biopotential signals from the user and transmitting these to the processing device 23. This may enable the synchronised output signals to be provided immediately or with a very small delay. In other examples the synchronisation may be performed at a later time.

In some examples the biopotential signals that are synchronised comprise further biopotential signals detected by the first capacitive sensor 29 and the second capacitive sensor 29. For example, the first biopotential signal and the second biopotential signal may be used to calibrate the system 21 and determine how the synchronisation should be performed. Once the system 21 has been calibrated the capacitive sensors 29 may then be used to obtain further biopotential signals which can then be synchronised as required.

In some examples one or more of the capacitive sensors 29 may be moved between the block 31 of obtaining the calibration biopotential signals and the block 33 of obtaining the further biopotential signals. For instance, to obtain the calibration biopotential signals the capacitive sensors 29 may be positioned on the torso of a subject 27 and then the capacitive sensor 29 could be positioned on the subject's 27 head to obtain the further biopotential signals.

In some examples the calibration biopotential signals and the further biopotential signals may comprise information about different types of biopotentials. In some examples the calibration biopotential signals may comprise signals that comprise distinctive features that can be easily recognised by the processing circuitry 5 while the further biopotential signals may comprise features that are not as easily recognised by the processing circuitry 5. For instance the first biopotential signal and the second biopotential signal that are used as the calibration signals could comprise ECG signals and the further biopotential signals could comprise electrooculogram (EOG) signals or vice versa. It is to be appreciated that other types of biopotential signals could be used in other examples of the disclosure. Other types of biopotential signals could comprise electroencephalogram signals, electronystagmogram signals, electromyogram signals, electroneurogram signals, or skin potentials or other types of signals.

In some examples of the disclosure once the biopotential signals have been synchronised they may be processed. The processing may be performed by the processing circuitry 5 of the processing device 23. In some examples the biopotential signals may be transmitted to one or more other processing devices 23 to enable the processing to be performed. The processing may comprise removing noise from one or more of the biopotential signals and/or reconstructing at least part of the one or more biopotential signals and/or any other suitable processing.

The reconstruction of the biopotential signals may comprise any suitable method which enables a partial signal to be reconstructed. In some examples a machine learning process may be used to enable the reconstruction of at least part of the biopotential signals. In such examples the processing circuitry 5 may use signals that are stored in the database 13 to enable the missing segments of the obtained biopotential signals to be identified and reconstructed.

In some examples the processing of the biopotential signals may enable feedback to be provided to the subject 27 or another user of the system 21 such as a medical professional. For instance, if the biopotential signals comprise information indicative of the user's heart rate then the processing of the signal may enable information indicative of the heart rate to be provided. In some examples the system 21 may be arranged to give a warning output if the heart rate drops outside of a threshold frequency band.

In the example method described above the method comprises receiving two biopotential signals from two capacitive sensors 29. It is to be appreciated that in implementations of the disclosure the method may comprise receiving the biopotential signals from more than two capacitive sensors 29. For example a plurality of capacitive sensors 29 may be positioned at a plurality of different locations on the subject 27. Each of the capacitive sensors 29 may be operating independently of the other capacitive sensors 29 so that there is no direct communication between any of the capacitive sensors 29.

In some examples one or more of the capacitive sensors 29 may act as a gateway for one or more other capacitive sensors 29 within the system 21. For example a communication link may be established between a first capacitive sensor 29 and a second capacitive sensor 29. This may enable information to be provided from the first capacitive sensor 29 to the second capacitive sensor 29. The second capacitive sensor 29 may then use a communication link 28 to transmit the information to a processing device 23.

In some examples the processing device 23 may be arranged to provide control signals to one or more of the capacitive sensors 29. The processing device 23 may provide the control signals via the wireless communication links 28. The control signals may control the time periods for which the capacitive sensors 29 are active. This may enable different capacitive sensors 29 to be active for different time periods. For example a first control signal, provided to a first capacitive sensor 29, may cause the first capacitive sensor 29 to be active for a first time period and inactive for a second time period while a second control signal, provided to a second capacitive sensor 29, may cause the second capacitive sensor 29 to be inactive for the first time period and active for the second time period. This enables different capacitive sensors 29 to detect the biopotential signals at different times. In such examples a machine learning algorithm may be used to reconstruct the signals to correct for the time periods where the capacitive sensors 29 are inactive.

Having different capacitive sensors 29 active at different times may provide for a more efficient sensing system 21 because it reduces the power requirements of the system. Having reduced power requirements may also enable the capacitive sensors 29 to be worn for a longer period of time and so may enable the information about the biopotential signals to be obtained over longer periods of time. This may also reduce the amount of data that is collected and so reduces the bandwidth required for the communication links 28 and may reduce the processing requirements and/or memory requirements for the processing device 23.

In some examples the control signals may also allow for adaptive operation of the capacitive sensors 29. For example, the processing device 23 may be arranged to determine optimal operating variables for the capacitive sensors 29 and transmit these to the capacitive sensors 29 via the communication links 28. The operative variables that are controlled by the control signals could comprise the filters used, the gain applied or any other suitable variables.

FIG. 4 illustrates another method which may be implemented using apparatus 1 and systems 21 as described.

At block 41 a plurality of biopotential signals are received. In the example method of FIG. 4 in biopotential signals are received. The n biopotential signals may be received from n capacitive sensors 29 which may be as described above. Each of the biopotential signals may comprise time as one of the dimensions.

At block 43 the method comprises synchronizing the received biopotential signals. The received biopotential signals could be synchronized using any suitable method. In the example method of FIG. 4 the biopotential signals may be synchronized by extracting features in the received biopotential signals and using these extracted features to determine the time delay. The biopotential signals can then be synchronized by adding the suitable delay to the respective biopotential signals.

At block 45 the method comprises dimensionality reduction. The dimensionality reduction may ensure that the dimensionality of the output signals is fixed for any number of input biopotential signals. The dimensionality reduction may be implemented using principal components analysis, independent components analysis, singular value decomposition, machine learning or any other suitable process.

At block 47 the synchronized biopotential signals are processed.

In some examples the processing performed at block 47 comprises reducing the noise in the synchronized biopotential signal. The noise that is present in the received biopotential signals could comprise noise caused by internal sources and/or noise caused by external sources. The internal sources may be internal to the body of the subject 27. The internal sources of noise could be caused by motion of the subject 27, muscle signals, poor electrical connection between the capacitive sensors 29 and the subject 27 or any other suitable source. The external sources of noise could be caused by powerline noise or any other suitable source.

In the example method of FIG. 4 the processing may comprise machine learning processes. In such examples the machine learning process may enable the biopotential signals to be retrieved from noisy and/or partial signals. This may require machine learning information to be obtained from one or more databases 13. The machine learning information 48 that is retrieved from the one or more databases may comprise information 48 that has been obtained from a plurality of subjects 27. In some examples the machine learning information 48 may comprise a high quality signal. The high quality signal could be obtained using a different system 21 to the one used to obtain the biopotential signals in examples of the disclosure. The high quality signal could be obtained using a more reliable and less noisy system. The information from the high quality signals can be used to reconstruct the noisy and/or partial biosignals obtained from the capacitive sensors 29.

In some examples the machine learning information 48 may be obtained from the same subject 27 being currently monitored. In some examples the machine learning information 48 could also comprise, or alternatively comprises, data obtained from one or more other subjects. The machine learning information 48 may be determined by using corresponding pairs of input signal and output signal examples to obtain a generalized mapping between them.

The machine learning process may be implemented using fully connected, recurrent or one dimensional convolutional neural network or by using support vector machines using features obtained by discrete cosine transforms, fast Fourier transforms or wavelets or by using any other suitable process.

For instance deep convolutional neural networks can be used as a model between input signals and output signals. The machine learning can be trained using any variant of stochastic gradient descent, where random corresponding pairs of input and output data are shown sequentially to the machine learning training process. The machine learning training process then computes a predicted output and error between predicted output and target output. In some examples error gradients may then be computed with regards to the neural networks weights, and then the weights are adjusted in order to minimize the error between target output and the predicted output. The machine learning training process continues until the model converges or some other external criteria is met. After training, the machine learning process can be used for prediction.

In some examples the machine learning process may also comprise calculating a confidence estimate. This may provide an indication of the amount of error in the processed signal.

At block 49 an output signal is obtained. In some examples the output signal is the synchronized biopotential signals. In other examples the output signals may comprise a signal derived from the synchronized biopotential signals. For example, the input biopotential signal could comprise an ECG signal and the output signal could comprise the subject's heart rate or heart rate variability.

In the described examples each of the capacitive sensors 29 may have the same clock speed, however, as the capacitive sensors 29 are operating independently of each other different capacitive sensors 29 may have different reference times. The above described examples enable the reference times to be synchronised by post-processing. In other examples the capacitive sensors 29 could have different clock speeds. In such examples additional processes may be used to account for the differences in clock speeds. For examples, dynamic time warping distance based methods or machine learning processes may be used to enable the time alignment between the different capacitive sensors 29.

A technical effect of one or more examples described herein is providing a wireless system 21 which can be used to monitor biopotential signals from a subject. As the system is wireless 21 this means that the capacitive sensors 29 can be positioned on any suitable location on the subject. This may enable different types of biopotential signals to be monitored. This may also allow freedom of movement for the subject 27 while the biopotential signals are being measured.

Examples of the disclosure may also enable different types of data to be extracted from biopotential signals. For instance in some examples it may enable both ECG and EOG data to be extracted from the same biopotential signals. This may allow for improved medical diagnostics which may reduce the number of capacitive sensors 29 needed and/or the amount of tests that are required on the subject 27.

In this description the term coupled means operationally coupled and any number or combination of intervening elements can exist between coupled components (including no intervening elements).

The term "comprise" is used in this document with an inclusive not an exclusive meaning. That is any reference to X comprising Y indicates that X may comprise only one Y or may comprise more than one Y. If it is intended to use 'comprise' with an exclusive meaning then it will be made clear in the context by referring to "comprising only one . . . " or by using "consisting".

In this brief description, reference has been made to various examples. The description of features or functions in relation to an example indicates that those features or functions are present in that example. The use of the term "example" or "for example" or "may" in the text denotes, whether explicitly stated or not, that such features or functions are present in at least the described example, whether described as an example or not, and that they can be, but are not necessarily, present in some of or all other examples. Thus "example", "for example" or "may" refers to a particular instance in a class of examples. A property of the instance can be a property of only that instance or a property of the class or a property of a sub-class of the class that includes some but not all of the instances in the class. It is therefore implicitly disclosed that a feature described with reference to one example but not with reference to another example, can where possible be used in that other example but does not necessarily have to be used in that other example.

Although embodiments of the present invention have been described in the preceding paragraphs with reference to various examples, it should be appreciated that modifications to the examples given can be made without departing from the scope of the invention as claimed.

Features described in the preceding description may be used in combinations other than the combinations explicitly described.

Although functions have been described with reference to certain features, those functions may be performable by other features whether described or not.

Although features have been described with reference to certain embodiments, those features may also be present in other embodiments whether described or not.

Whilst endeavoring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

We claim:
1. A method comprising:
receiving a first biopotential signal obtained by a first capacitive sensor;
receiving a second biopotential signal obtained by a second capacitive sensor, the first capacitive sensor and the second capacitive sensor being positioned at different locations on a subject;
comparing reference signals of a database to the received first biopotential signal and second biopotential signal to enable the biopotential signals to be synchronized using a machine learning algorithm;
synchronising biopotential signals obtained by the first capacitive sensor and the second capacitive sensor by applying a time adjustment to biopotential signals obtained by at least one of the first capacitive sensor or the second capacitive sensor;
wherein features in at least one of the first biopotential signal and the second biopotential signal are used to synchronise the biopotential signals obtained by the first capacitive sensor and the second capacitive sensor.

2. A method as claimed in claim 1, wherein synchronising the biopotential signals comprises determining a delay between the first biopotential signal and the second biopotential signal.

3. A method as claimed in claim 1, wherein synchronising the biopotential signals comprises combining the first biopotential signal and the second biopotential signal and adjusting the time alignment of the biopotential signals to provide a combined signal comprising features.

4. A method as claimed in claim 3, comprising:
using a machine learning process to recognise the features.

5. A method as claimed in claim 1, wherein the biopotential signals that are synchronised comprise the first biopotential signal and the second biopotential signal.

6. A method as claimed in claim 1, wherein the biopotential signals that are synchronised comprise further biopotential signals detected by the first capacitive sensor and the second capacitive sensor.

7. A method as claimed in claim 6, wherein the first biopotential signal and the second biopotential signal comprise information indicative of a first type of biopotential and the further biopotential signals detected by the first capacitive sensor and the second capacitive sensor comprise information indicative of a second different type of biopotential.

8. A method as claimed in claim 7, wherein the first biopotential signal and the second biopotential signal comprise electrocardiogram signals and the further biopotential signals comprise at least one of; electroencephalogram signals, electro-oculogram signals, electronystagmogram signals, electromyogram signals, electroneurogram signals, or skin potentials.

9. A method as claimed in claim 1, comprising:
causing processing of the synchronised biopotential signals wherein the processing comprises at least one of; removing noise from one or more of the biopotential signals, reconstructing at least part of the one or more biopotential signals.

10. A method as claimed in claim 9, wherein a machine learning process is used to reconstruct at least part of the one or more biopotential signals.

11. A method as claimed in claim 1, wherein the biopotential signals obtained by the first capacitive sensor and the second capacitive sensor are received via wireless communication links.

12. A method as claimed in claim 1, wherein the biopotential signals are obtained from more than two capacitive sensors.

13. A method as claimed in claim 1, comprising:
providing a control signal for at least one of the capacitive sensors wherein the control signal causes the at least one capacitive sensor to be active for a first time period and inactive for a second time period.

14. A method as claimed in claim 1, comprising:
providing control signals to the capacitive sensors so that different capacitive sensors are arranged to detect the biopotentials at different times.

15. An apparatus, comprising:
at least one processor; and
at least one non-transitory memory including computer program code wherein the at least one non-transitory memory and the computer program code are configurated, with the at least one processor, cause the apparatus at least to perform:
receiving a first biopotential signal obtained by the first capacitive sensor;
receiving a second biopotential signal obtained by a second capacitive sensor, the first capacitive sensor and the second capacitive sensor being positioned at different locations on a subject;
comparing reference signals of a database to the received first biopotential signal and second biopotential signal to enable the biopotential signals to be synchronized using a machine learning algorithm;
synchronising biopotential signals obtained by the first capacitive sensor and the second capacitive sensor by applying a time adjustment to biopotential signals obtained by at least one of the first capacitive sensor or the second capacitive sensor;
wherein features in at least one of the first biopotential signal and the second biopotential signal are used to synchronize the biopotential signals obtained by the first capacitive sensor and the second capacitive sensor.

16. An apparatus as claimed in claim 15, wherein synchronising the biopotential signals comprises determining a delay between the first biopotential signal and the second biopotential signal.

17. An apparatus as claimed in claim 15, wherein synchronising the biopotential signals comprises combining the first biopotential signal and the second biopotential signal and adjusting the time alignment of the biopotential signals to provide a combined signal comprising features.

18. An apparatus as claimed in claim 15, wherein the biopotential signals obtained by the first capacitive sensor and the second capacitive sensor are received via wireless communication links.

19. An apparatus as claimed in claim 15, wherein the biopotential signals are obtained from more than two capacitive sensors.

20. An apparatus as claimed in claim 15, wherein the at least one non-transitory memory including computer program code is configured with the at least one processor to cause the apparatus to perform:
providing a control signal for at least one of the capacitive sensors wherein the control signal causes the at least one capacitive sensor to be active for a first time period and inactive for a sec.

* * * * *